(12) United States Patent
Watanabe et al.

(10) Patent No.: US 6,660,295 B2
(45) Date of Patent: *Dec. 9, 2003

(54) TRANSDERMAL DRUG DELIVERY DEVICE PACKAGE WITH IMPROVED DRUG STABILITY

(75) Inventors: Tyler Watanabe, Los Altos, CA (US); Robert M. Gale, Los Altos, CA (US)

(73) Assignee: Alza Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,534

(22) Filed: Sep. 29, 1998

(65) Prior Publication Data

US 2001/0051180 A1 Dec. 13, 2001

Related U.S. Application Data

(60) Provisional application No. 60/060,397, filed on Sep. 30, 1997.

(51) Int. Cl.[7] .................................................. A61F 13/00
(52) U.S. Cl. ........................................ 424/448; 424/449
(58) Field of Search ................................... 424/448, 449

(56) References Cited

U.S. PATENT DOCUMENTS

| | | | |
|---|---|---|---|
| 3,426,754 A | 2/1969 | Bierenbaum et al. | 128/156 |
| 3,598,123 A | 8/1971 | Zaffaroni | 128/268 |
| 3,731,683 A | 5/1973 | Zaffaroni | 128/268 |
| 3,797,494 A | 3/1974 | Zaffaroni | 128/268 |
| 3,991,755 A | 11/1976 | Vernon et al. | 128/172.2 |
| 4,031,894 A | 6/1977 | Urquhart et al. | 128/268 |
| 4,141,359 A | 2/1979 | Jacobsen et al. | 128/172.1 |
| 4,201,211 A | 5/1980 | Chandrasekaran et al. | 128/268 |
| 4,250,878 A | 2/1981 | Jacobsen et al. | 128/207.21 |
| 4,274,420 A | 6/1981 | Hymes | 128/641 |
| 4,286,592 A | 9/1981 | Chandrasekaran | 128/260 |
| 4,299,719 A | 11/1981 | Aoki et al. | 252/188 |
| 4,314,557 A | 2/1982 | Chandrasekaran | 128/260 |
| 3,598,122 | 11/1982 | Zaffaroni | 128/268 |
| 4,379,454 A | 4/1983 | Campbell et al. | 604/897 |
| 4,435,180 A | 3/1984 | Leeper | 604/896 |
| 4,524,015 A | 6/1985 | Takahashi et al. | 252/188.28 |
| 4,559,222 A | 12/1985 | Enscore et al. | 424/28 |
| 4,568,343 A | 2/1986 | Leeper et al. | 604/896 |
| 4,588,580 A | 5/1986 | Gale et al. | 424/21 |
| 4,638,043 A | 1/1987 | Szycher et al. | 528/75 |
| 4,640,689 A | 2/1987 | Sibalis | 604/20 |
| 4,645,502 A | 2/1987 | Gale et al. | 604/896 |
| 4,698,062 A | 10/1987 | Gale et al. | 604/896 |
| 4,702,732 A | 10/1987 | Powers et al. | 604/20 |
| 4,704,282 A | 11/1987 | Campbell et al. | 424/449 |
| 4,725,272 A | 2/1988 | Gale | 424/448 |
| 4,747,845 A | 5/1988 | Korol | 604/368 |
| 4,781,924 A | 11/1988 | Lee et al. | 424/449 |
| 4,784,857 A | 11/1988 | Berry et al. | 424/449 |
| 4,788,062 A | 11/1988 | Gale et al. | 424/449 |
| 4,816,258 A | 3/1989 | Nedberge et al. | 424/448 |
| 4,849,226 A | 7/1989 | Gale | 424/448 |
| 4,904,475 A | 2/1990 | Gale et al. | 424/449 |
| 4,908,027 A | 3/1990 | Enscore et al. | 604/890 |
| 4,917,895 A | 4/1990 | Lee et al. | 424/448 |

(List continued on next page.)

*Primary Examiner*—Shelley A. Dodson
(74) *Attorney, Agent, or Firm*—Vandana Date

(57) ABSTRACT

This invention relates to the field of transdermal drug delivery devices and more particularly to improved storage stability thereof. The invention comprises providing a transdermal drug delivery device with a non-occlusive backing or release liner in combination with a degradation protectant such as a desiccant or oxygen scavenger within the sealed pouch containing the device. The combination of the present invention provides increased shelf-life of these devices.

16 Claims, 1 Drawing Sheet

U.S. PATENT DOCUMENTS

| | | | |
|---|---|---|---|
| 4,928,680 A | 5/1990 | Sandbank | 128/155 |
| 4,938,759 A | 7/1990 | Enscore et al. | 604/896.1 |
| 4,943,435 A | 7/1990 | Baker et al. | 424/448 |
| 4,992,410 A | 2/1991 | Cullen et al. | 502/407 |
| 4,994,278 A | 2/1991 | Sablotsky et al. | 424/449 |
| 5,004,610 A | 4/1991 | Osborne et al. | 424/448 |
| 5,071,656 A | 12/1991 | Lee et al. | 424/448 |
| 5,077,104 A | 12/1991 | Hunt et al. | 428/34.3 |
| 5,141,750 A | 8/1992 | Lee et al. | 424/448 |
| 5,143,769 A | 9/1992 | Moriya et al. | 428/76 |
| 5,207,943 A | 5/1993 | Cullen et al. | 252/188.28 |
| 5,208,431 A | 5/1993 | Uchiyama et al. | 219/121.65 |
| 5,223,261 A | 6/1993 | Nelson et al. | 424/443 |
| 5,242,433 A | 9/1993 | Smith et al. | 604/289 |
| 5,258,179 A | 11/1993 | Bracco et al. | 424/94.1 |
| 5,262,375 A | 11/1993 | McKedy | 502/406 |
| 5,268,209 A | 12/1993 | Hunt et al. | 428/34.4 |
| 5,332,590 A | 7/1994 | McKedy | 426/398 |
| 5,342,623 A | 8/1994 | Enscore et al. | 424/448 |
| 5,352,456 A | 10/1994 | Fallon et al. | 424/448 |
| 5,362,501 A | 11/1994 | Gopeland et al. | 426/12 |
| 5,364,555 A | 11/1994 | Zenner et al. | 252/188.28 |
| 5,411,740 A | 5/1995 | Lee et al. | 424/448 |
| 5,411,750 A | 5/1995 | Lajoie et al. | 424/717 |
| 5,500,222 A | 3/1996 | Lee et al. | 424/448 |
| 5,536,263 A | 7/1996 | Rolf et al. | 604/307 |
| 5,614,211 A | 3/1997 | Gale et al. | 424/448 |
| 5,635,203 A | 6/1997 | Gale et al. | 424/448 |
| 5,698,217 A | 12/1997 | Wilking | 424/448 |

TRANSDERMAL DRUG DELIVERY DEVICE PACKAGE WITH IMPROVED DRUG STABILITY

This is a provisional of application No. 60/060,397 filed on Sep. 30, 1997.

FIELD OF THE INVENTION

This invention relates to transdermal drug delivery devices and more particularly, to a method for protecting such devices from degradation such as that due to hydrolysis and/or oxidation during storage.

BACKGROUND OF THE INVENTION

The transdermal route of parenteral drug delivery provides many advantages over other administrative routes. Transdermal drug delivery devices, including multilaminates and monoliths, for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,588,580; 4,645,502; 4,698,062; 4,704,282; 4,725,272; 4,781,924; 4,788,062; 4,816,258; 4,849,226; 4,904,475; 4,908,027; 4,917,895; 4,938,759; 4,943,435; 5,004,610; 5,071,656; 5,141,750; 5,342,623; 5,411,740; and 5,635,203, all of which are hereby incorporated in their entirety by reference.

Drugs may also be administered transdermally by iontophoresis, and iontophoretic delivery devices for delivering a wide variety of drugs of other beneficial agents are well known in the art. Iontophoretic devices include a donor electrode assembly which includes a donor electrode and a reservoir containing the beneficial agent to be iontophoretically delivered. The device also includes a counter electrode assembly and an electric power source. Typical devices are disclosed in U.S. Pat. Nos. 3,991,755, 4,141,359, 4,250,878, 4,274,420, 4,640,689, and 4,702,732, for example, all of which are incorporated herein by reference.

One problem associated with the devices of the prior art is degradation of the contents of the device, such as the drugs, permeation enhancers, matrix materials, or other components contained therein. Degradation not only undesirably breaks down these materials, but it also causes discoloration and formation of odors within the pouched system. Devices susceptible to degradation can not be stored for a reasonable amount of time, thus causing practical problems in their distribution.

A solution disclosed in the prior art is to incorporate an antioxidant into the device. For example, U.S. Pat. Nos. 5,028,431 and 5,242,433, hereby incorporated in their entirety by reference, disclose mixing antioxidants such as BHT into the drug formulation of a transdermal drug delivery device due to the unstable nature of the drug to be delivered.

Another solution has been to incorporate a desiccant material within the sealed pouch containing the transdermal drug delivery device. For example, the Climara® transdermal estradiol system is packaged and sold within a sealed pouch containing a water scavenger to protect against hydrolysis of estradiol. This system is disclosed in U.S. Pat. No. 5,223,261 and the dessicant containing package is disclosed in U.S. Pat. No. 5,698,217, which are hereby incorporated in their entirety by reference.

Transdermal drug delivery systems typically comprise at a minimum a drug reservoir layer covered or surrounded by a backing layer and a release liner. The backing layer may be occlusive or non-occlusive. For example, the Climara® system comprises a polyethylene backing layer having a low moisture vapor transmission rate (MVTR) of approximately 7–11 $g/m^{2\cdot}$ 24 hr. More open backing layers such as spun laced polyester (Sontara®) are disclosed in U.S. Pat. Nos. 5,411,750, 5,500,222, and 5,614,211, which are incorporated herein by reference. Other non-occlusive backing layers are disclosed in U.S. Pat. Nos. 3,426,754, 4,638,043, 4,994,278, 5,352,456, and 5,536,263, all of which are hereby incorporated in their entirety by reference.

We have found that even when placed in pouches containing degradation protectants such as antioxidants and desiccants, certain transdermal delivery devices still degrade at rates higher than desirable. Thus, there is a need for improved storage stability of such devices.

DEFINITION OF TERMS

As used herein, the term "degradation" refers to any change in any of the device components during storage, for example by hydrolysis and/or oxidation of the drug, permeation enhancers, matrix materials, and any other excipients contained within the device.

As used herein, the term "degradation agent" refers to any agent within the device or pouch which causes an undesirable by-product, such as water and/or oxidizing agents.

As used herein, the term "degradation protectant" refers to any material which protects against degradation of any of the device components such as water scavengers, oxygen scavengers, or combinations thereof.

As used herein, the term "non-occlusive" refers to a material having a moisture vapor transmission rate (MVTR) of not less than 20 $g/m^2.24$ hr.

SUMMARY OF THE INVENTION

We have found that many transdermal drug delivery devices contain degradation agents that must be removed or scavenged from the device in order to maintain stability. When impermeable backings are used, the only pathway which these materials can be exposed to the degradation protectant is through the unsealed edges of the device. Diffusion through this pathway is very slow.

According to our invention, we have found that stability of such devices can be considerably improved when stored in pouches containing degradation protectants if the transdermal device uses a non-occlusive backing.

Accordingly, it is an aspect of this invention to provide an improved method for preventing degradation of the components of transdermal drug delivery devices.

It is another aspect of this invention to provide an improved packaged transdermal drug delivery device comprising a transdermal drug delivery device having a non-occlusive backing layer contained within a sealed pouch containing a degradation protectant.

It is another aspect to increase the shelf-life of a transdermal drug delivery device.

It is yet another aspect of this invention to provide improved packaged oxybutynin transdermal drug delivery systems.

The present invention comprises a combination of a transdermal drug delivery device having a non-occlusive backing layer wherein the device is sealed within a pouch containing a degradation protectant. The combination of the non-occlusive backing layer and the degradation protectant within the sealed pouch protects the contents of the transdermal drug delivery device from degradation.

DETAILED DESCRIPTION OF THE INVENTION

Figure 1:
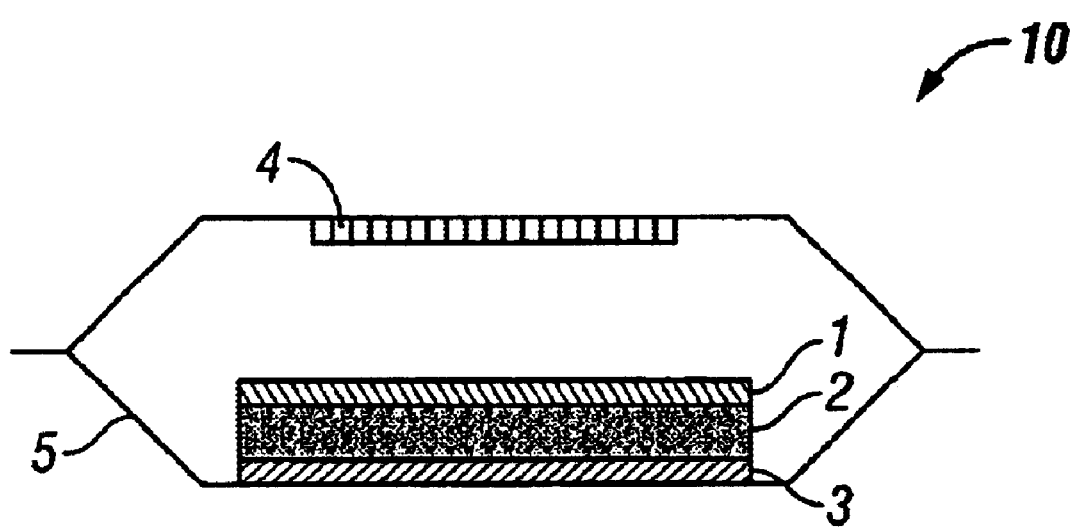
FIG. 1 depicts a cross-sectional view of one embodiment of this invention.

According to the present invention, an improved packaged transdermal drug delivery device and method for preventing degradation thereof are provided. The improvement comprises providing a transdermal drug delivery device with a non-occlusive backing in combination with incorporating a degradation protectant into the pouch containing the device. The resultant combination provides improved protection against degradation of the contents of the delivery device, thereby increasing the shelf-life of such devices.

With reference to FIG. 1, the packaged transdermal drug delivery device 10 includes backing layer 1, drug reservoir layer 2, and release liner 3 which make up the drug delivery device. The device is packaged within pouch 5 which also includes degradation protectant 4. Alternately, the device may include additional layers such as a rate control membrane (not shown) or in-line contact adhesive (not shown) as known in the art.

The porosity of the backing layer must be sufficient to allow the degradation agents and products within the delivery device to readily diffuse through the backing layer. This is necessary to enable the degradation agents and products located at or near the center of the device to diffuse through the system backing to be absorbed by the degradation protectant. If the backing layer is too occlusive, the only available path for diffusion of the degradation agents contained within the device is through the system edges. This may not be sufficient to allow all the degradation agents products located at or near the center of the device to diffuse through the system to be absorbed by the degradation protectant.

The non-occlusive backings of the present invention comprise a MVTR of greater than about 20 g/m$^2$.24 hr and are preferably within the range of human skin of about 70–150 g/m$^2$.24 hr. Backings having a MVTR within the range of human skin are preferred as they also result in enhanced adhesion of some devices, particularly those comprising surfactant-like permeation enhancers. Backings with a higher MVTR can also be utilized in accordance with the present invention.

Suitable backing layer materials include woven or non-woven materials. For example and not by way of limitation, non-woven materials include spun-laced or spun-bonded polyester, polyethylene or polypropylene and the like, microporous or macroporous polyester, polypropylene, or polyethylene and the like, rayon, polyester/rayon, and polypropylene/rayon. Woven materials include, for example, cloth, nylon and nylon/rayon taffeta.

According to another embodiment of this invention, the desired porosity of the backing layer may be derived by piercing the backing layer with a predetermined number of holes. This may be done, for example, by firmly applying a backing layer against a substrate comprising an array of piercing elements. The array of piercing elements may be selected to provide the desired porosity. According to this embodiment, backing layers which are otherwise too occlusive may be rendered suitable for practice of this invention.

The combination device and package of the present invention protects against degradation of any of the components of the transdermal drug delivery device, such as the drug, permeation enhancers, and any potential by-products. For example, esters can undergo acid or base catalyzed hydrolysis and/or trans-esterification which result in the formation of breakdown products of the corresponding acid and alcohol. Practice of this invention is not to be limited to any particular drug, permeation enhancer, or other excipient. However, devices containing labile ester drugs and permeation enhancers, such as fatty acid esters, are particularly suited for practice of this invention.

Examples of drugs include estradiol, fluoxetine, paroxetine, and ester drugs such as oxybutynin.

Examples of permeation enhancers include monoglycerides or mixtures of monoglycerides of fatty acids having a total monoesters content of at least 51% wherein the monoesters are those with from 10–20 carbon atoms such as glycerol monolaurate, glycerol monooleate, and glycerol monolinoleate, fatty acids and esters of fatty acids having from about 10 to about 20 carbon atoms, polyethylene glycol monolaurate, and combinations thereof. Fatty acids are, for example, lauric acid, myristic acid, stearic acid, oleic acid, linoleic acid, and palmitic acid and fatty acid esters include, for example, lauryl lactate, isopropyl myristate, dodecyl acetate, ethyl palmitate, and methyl laurate.

The degradation protectants for use with the present invention are known in the art. Suitable degradation protectants are disclosed in, for example and not by way of limitation, U.S. Pat. Nos. 4,299,719, 4,524,015, 4,992,410, 5,143,769, 5,207,943, 5,258,179, 5,262,375 5,332,590, 5,362,501, and 5,364,555, which are hereby incorporated in their entirety by reference. Preferred water scavengers include anhydrous calcium sulfate such as Drierite®, anhydrous silica gel powders such as Natrasorb™, and Desimax® produced by Multiform Technologies. A preferred water and oxygen scavenger is Freshpax™ produced by Multiform Technologies. The amount of degradation protectant required depends on the volume of the protected space and the expected water content of the drug delivery device, with sufficient overcapacity, and may readily be determined by one of ordinary skill.

The pouch material is selected from materials known in the art. It is preferred that that pouch material is self-sealable and acts as a barrier to the drug contained within the device. For example, suitable pouch materials are disclosed in U.S. Pat. Nos. 5,077,104 and 5,268,209, which are hereby incorporated in their entirety by reference.

A preferred embodiment is directed to transdermal drug delivery devices for administering oxybutynin. Such devices are disclosed in U.S. Pat. Nos. 5,411,750, 5,500,222, and 5,614,211, listed above, and are also disclosed in U.S. Pat. Nos. 4,747,845, 4,784,857, and 4,928,680, which are hereby incorporated in their entirety by reference. The present inventors have found that oxybutynin within such systems breaks down to oxybutynin-N-oxide, a yellowish by-product. According to this preferred embodiment, a degradation protectant which is both a water and oxygen scavenger is sealed within the pouch. The backing is preferably spun-laced polyester such as Sontara® manufactured by DuPont of Wilmington, Del.

Although the invention has been described with respect to the use of a non-occlusive backing, a non-occlusive release liner could also be used in those cases where the use of the device may require an occlusive backing.

The aforementioned patents describe a wide variety of materials for fabricating the various layers or components of transdermal drug delivery devices for use according to this invention. This invention therefore contemplates the use of materials other than those specifically disclosed herein, including those which may hereafter become known to the art to be capable of performing the necessary functions. The following example is intended to illustrate the practice of this invention and is not intended to limit the invention in any manner.

EXAMPLE 1

An oxybutynin/permeation enhancer reservoir is prepared by mixing ethylene vinyl acetate copolymer having a vinyl acetate content of 40 percent in an internal mixer (Brabender type mixer) until the EVA 40 pellets are fused. Oxybutynin, glycerol monolaurate, and a fatty acid ester cosolvent such as dodecyl acetate are then added. The mixture is blended, cooled and calendered to a 5 mil thick film.

The drug reservoir film is then laminated to a spun-laced polyester backing layer such as a Sontara® backing (DuPont, Wilmington, Del.) on its skin distal surface and a Celgard microporous polypropylene membrane tie layer on its skin facing surface. A contact adhesive is then laminated to the microporous polypropylene tie layer and an impermeable release liner is laminated to the contact adhesive.

A packet containing degradation protectant such as Freshpax™ (Multiform Technologies, Buffalo, N.Y.) is adhered to the inside of a pouch. The multilaminate device is then placed within the pouch and the pouch is sealed, for example, by heat sealing.

This invention has been described in detail with particular reference to certain preferred embodiments thereof, but it will be understood that variations and modifications can be effected within the spirit and scope of this invention.

What is claimed is:

1. A package for a transdermal drug delivery device comprising, in combination:
    a pouch containing:
        (a) a transdermal drug delivery device comprising a drug reservoir layer positioned between a release liner and a backing layer, at least one of said release liner and said backing layer being non-occlusive;
        (b) a degradation protectant.

2. The combination of claim 1 wherein the non-occlusive layer comprises a moisture vapor transmission rate of at least 30 g/m².24 hr.

3. The combination of claim 1 wherein the non-occlusive layer comprises a moisture vapor transmission rate of about 70–150 g/m².24 hr.

4. The combination of claim 1 wherein the drug reservoir comprises drug dispersed within an adhesive layer.

5. The combination of claim 1 further comprising a contact adhesive layer between the drug reservoir and the release liner.

6. The combination of claim 1 wherein the degradation protectant is a water scavenger.

7. The combination of claim 1 wherein the degradation protectant is an oxygen scavenger.

8. The combination of claim 1 wherein the degradation protectant comprises a water scavenger and an oxygen scavenger.

9. The combination of claim 1 wherein the drug reservoir comprises oxybutynin.

10. The combination of claim 9 wherein the backing layer comprises spun-laced polyester.

11. The combination of claim 10 wherein the degradation protectant comprises an oxygen scavenger.

12. The combination of claim 11 wherein the degradation protectant additionally scavenges water.

13. A method for preventing degradation of a transdermal drug delivery device of the type comprising a drug reservoir positioned between a backing layer and a release liner comprising:
    (a) providing the transdermal drug delivery device with a non-occlusive backing layer or release liner comprising a moisture vapor transmission rate of at least 20 g/m².24 hr;
    (b) placing a degradation protectant within a pouch;
    (c) placing the device within the pouch;
    (d) sealing the pouch.

14. A method for increasing the shelf-life of a transdermal drug delivery device of the type comprising a drug reservoir positioned between a backing layer and a release liner comprising:
    (a) providing the transdermal drug delivery device with a non-occlusive backing layer or release liner comprising a moisture vapor transmission rate of at least 20 g/m².24 hr r;
    (b) placing a degradation protectant within a pouch;
    (c) placing the device within the pouch;
    (d) sealing the pouch.

15. The package of claim 1 wherein said transdermal drug delivery device contains at least one degradation agent.

16. The method of claim 14 wherein said transdermal drug delivery device contains at least one degradation agent.

* * * * *